(12) United States Patent
Lewandrowski et al.

(10) Patent No.: US 6,551,355 B1
(45) Date of Patent: Apr. 22, 2003

(54) TISSUE TRANSPLANT COATED WITH BIOCOMPATIBLE BIODEGRADABLE POLYMER

(75) Inventors: Kai-Uwe Lewandrowski, Brookline, MA (US); Shrikar Bondre, Malden, MA (US); Debra J. Trantolo, Princeton, MA (US); Maurice V. Cattaneo, Quincy, MA (US); Joseph D. Gresser, Brookline, MA (US); Donald L. Wise, Belmont, MA (US)

(73) Assignee: Cambridge Scientific, Inc., Cambridge, MA (US)

( * ) Notice: Subject to any disclaimer, the term of this patent is extended or adjusted under 35 U.S.C. 154(b) by 0 days.

(21) Appl. No.: 09/133,945

(22) Filed: Aug. 14, 1998

(51) Int. Cl.$^7$ .................................................. A61F 2/28
(52) U.S. Cl. ............................. 623/16.11; 623/23.63; 623/23.75
(58) Field of Search ................................ 623/16, 11, 66, 623/11.11, 16.11, 23.61, 23.63, 23.75, 23.72, 23.76, 23.51; 424/426; 435/325

(56) References Cited

U.S. PATENT DOCUMENTS

| | | | |
|---|---|---|---|
| 4,609,551 A | 9/1986 | Caplan et al. | 424/95 |
| 4,620,327 A | 11/1986 | Caplan et al. | 632/10 |
| 4,642,120 A | 2/1987 | Nevo et al. | 623/16 |
| 4,904,259 A | 2/1990 | Itay | 623/16 |
| 4,979,959 A | 12/1990 | Guire | 623/66 |
| 5,197,985 A | 3/1993 | Caplan et al. | 623/16 |
| 5,226,914 A | 7/1993 | Caplan et al. | 623/16 |
| 5,263,992 A | 11/1993 | Guire | 623/66 |
| 5,439,951 A | 8/1995 | Glimcher et al. | 523/115 |
| 5,518,680 A | 5/1996 | Cima et al. | 264/401 |
| 5,533,836 A | 7/1996 | Moore | 435/240.31 |
| 5,565,502 A | 10/1996 | Glimcher et al. | 523/115 |
| 5,626,861 A | 5/1997 | Laurencin et al. | 424/426 |
| 5,654,267 A | 8/1997 | Vuori et al. | 514/2 |
| 5,656,598 A | 8/1997 | Dunstan et al. | 514/12 |
| 5,700,289 A | * 12/1997 | Breitbart et al. | |
| 5,713,374 A | 2/1998 | Pachence et al. | 128/898 |
| 5,830,493 A | * 11/1998 | Yokota et al. | 623/23.61 |
| 5,866,415 A | * 2/1999 | Villeneuve | |
| 5,876,446 A | * 3/1999 | Agrawal et al. | 623/23.61 |
| 6,306,169 B1 | * 10/2001 | Lee et al. | 623/11.11 |

* cited by examiner

*Primary Examiner*—David J. Isabella
(74) *Attorney, Agent, or Firm*—Holland & Knight LLP

(57) ABSTRACT

A method by which immune responses to cortical bone grafts and other substrates (e.g., cement, IPN, etc.) can be minimized and at the same time graft osteoinductive potential can be improved, and improved graft substrate materials are disclosed. The method of the invention provides new types of bone grafts that incorporate into host bone more thoroughly and more rapidly, eliminating long-term complications, such as fracture, non-union, infection, and rejection. In the method of the invention, bone grafts or other substrates are modified to have an osteoinductive surface modification that the recipient's body will accept as its own tissue type and therefore will not reject or otherwise cause to fail. The osteoinductive surface modification comprises a biopolymer matrix coating that is seeded with periosteal cells that have been previously harvested either from the graft recipient or from an allogenic or xenogenic donor source.

11 Claims, 5 Drawing Sheets

TISSUE TRANSPLANT COATED WITH BIOCOMPATIBLE BIODEGRADABLE POLYMER

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The management of large skeletal defects continues to present a major challenge to orthopaedic surgeons, particularly when the problem arises in young patients in whom artificial devices and joint implants are likely to lead to early failure. Both cemented[111,145] and uncemented[60,75,139] devices have been shown to have significant and potential complications in young adults and children.

For example, there is a marked increase in the use of large frozen cortical bone allografts in limb-sparing procedures. These are used in the treatment of bone tumors[19,26,44,48,77,104,105,107,112,146,159], for repair of massive bone loss due to traumatic injury[69,99], in the treatment of avascular necrosis[12], and, increasingly, in failed joint arthroplasties, where extensive bone loss due to osteolysis is commonly encountered[47,56,76,109,125,130]. Even though the overall success rate for massive cortical bone allografts, as measured by return to work and engagement in relatively normal activities without crutches or braces, is approximately 75–85%, only 50% of these patients have an entirely uncomplicated postoperative course. About a quarter of the total group require reoperations such as autologous grafting or replating for stress fractures[4,5,32,103] or delayed unions[43,70,71,103-105,127]. Some patients require excision of the graft because of infection[98,149,150], reimplantation, long-term bracing or, in some cases, amputation. These results clearly indicate that problems still exist with this procedure and that if the technique is to be more widely applied, it must be more extensively examined and materially improved. Therefore, development of a biologic alternative seems eminently worthwhile.

SUMMARY OF THE INVENTION

The present invention provides a biologic alternative to be used in conjunction with artificial devices and joint implants for the purpose of reducing immune responses and fostering the incorporation of graft bone, and, in particular, cortical bone allografts, into the graft recipient's own bone. This approach can result in improvement of the clinical outcome of bone grafts and lower their complication rate.

In one aspect, the invention is directed to a composite biocompatible graft for cortical bone repair comprising a rigid biocompatible substratee having a porous biopolymer coating that is seeded with recipient periosteal cells. Preferably, the substrate material is a donor bone segment, e.g., a cortical bone allograft. In other embodiments, the allograft substrate material can be a resorbable precured bone cement, a molecularly reinforced interpenetrating network, a molded bioerodible polymer, or other similar materials.

The invention also relates to a grafting technique for promoting osteoinductivity and incorporation of a composite biocompatible bone graft in a lesion of a patient, comprising the steps of:

(a) producing a biocompatible graft substrate material; producing, in vitro, cultured periosteal cells derived from said patient;

(b) coating said biocompatible graft substrate material with a porous biopolymer matrix;

(c) seeding said polymer matrix on said biocompatible graft substrate material with said cultured periosteal cells to form a composite biocompatible graft having an activated matrix; and (d) implanting said composite biocompatible graft having said activated polymer matrix in said lesion.

Preferably, the polymer matrix is a polymer open-celled foam made from a bioerodible polymer such as poly(lactide-co-glycolide), which is also referred to as poly(lactic-co-glycolic) acid (PLGA; $H[-OCHR-CO-]OH$, $R=H$, $CH_3$), and preferably a PLGA having a lactide to glycolide ratio of 50:50, but may also include any lactide:glycolide ratio from 0:100 (i.e., poly(glycolide)) to 100:0 (i.e., poly(lactide)). The lactide moiety may be d,l-lactide or l-lactide. Other bioerodible polymers that may be useful in the invention include polydioxanone; poly(caprolactone); polyanhydride; poly(orthoester); poly(ether-co-ester); polyamide; polylactone; poly (propylene fumarate), $H[-O-CH(CH_3)-CH_2-O-CO-CH=CH-CO-]_nOH$; and combinations thereof. The thickness of the biopolymer foam coating ranges preferably from about 0.5 to about 1.5 millimeters, more preferably, from about 1 to about 2.5 millimeters. Adhesion of the polymer coating to the cortical bone graft is promoted by producing a surface roughness on the bone by grinding, laser ablation or other acceptable means.

The invention also relates to a biocompatible tissue transplant comprising a solid surface carrying a biopolymer coating to promote ingrowth of recipient tissues such as bone and blood vessels. The invention further relates to a tissue transplant of reduced immunogenicity comprising a solid surface carrying periosteal cells capable of regenerating autologous tissue.

The periosteal cells used in this invention are those that have been previously harvested either from the graft recipient or from allogenic or xenogenic donor sources. The periosteal cells are cultured in a matrix in media comprising inducers of osteogenesis selected from the group consisting of factors inducing bone formation, enzymes enhancing calcification, enzymes enhancing phosphorus deposition, vitamins, and prostaglandins.

The invention also encompasses a cortical bone allograft transplant for repair of bone defects comprising cells obtained by dissociating periosteal tissue, seeding periosteal cells on and in a biocompatible matrix suitable for repair of the defect, and culturing under culture conditions capable of inducing the periosteal cells to form new bone in the recipient of the transplant, thereby promoting incorporation in the transplant into the recipient's own bone.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
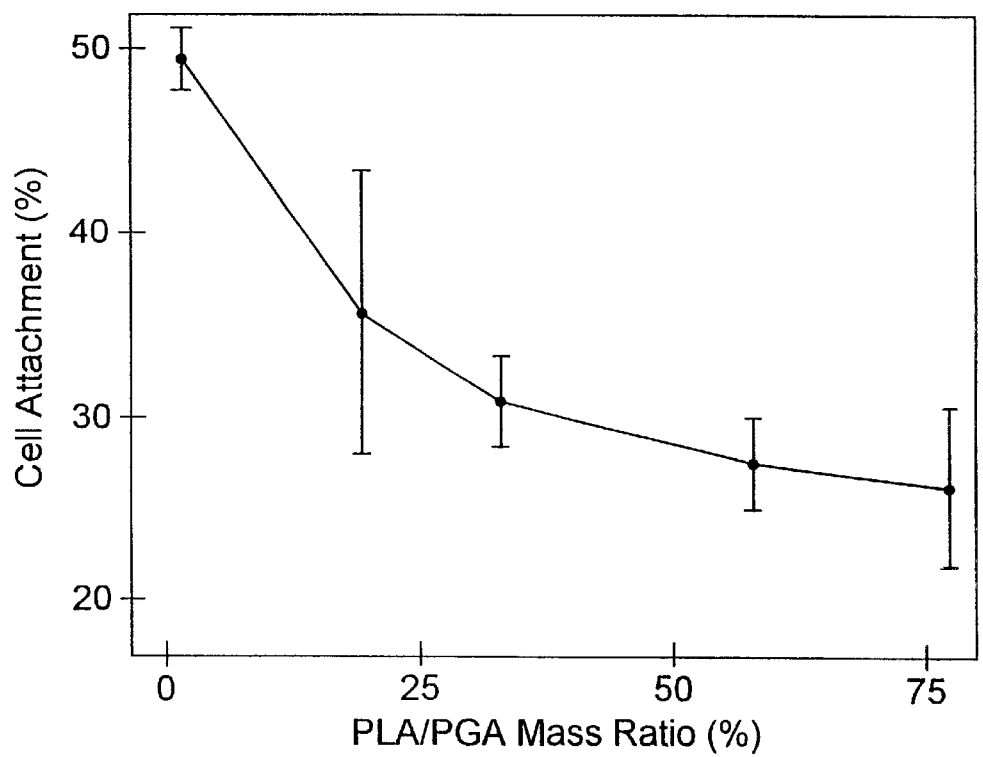
FIG. 1 is a graph showing the effect of PLA content on the percentage of cell seeding into the biopolymer matrix coating of a composite biocompatible graft of the invention.
Figure 2:
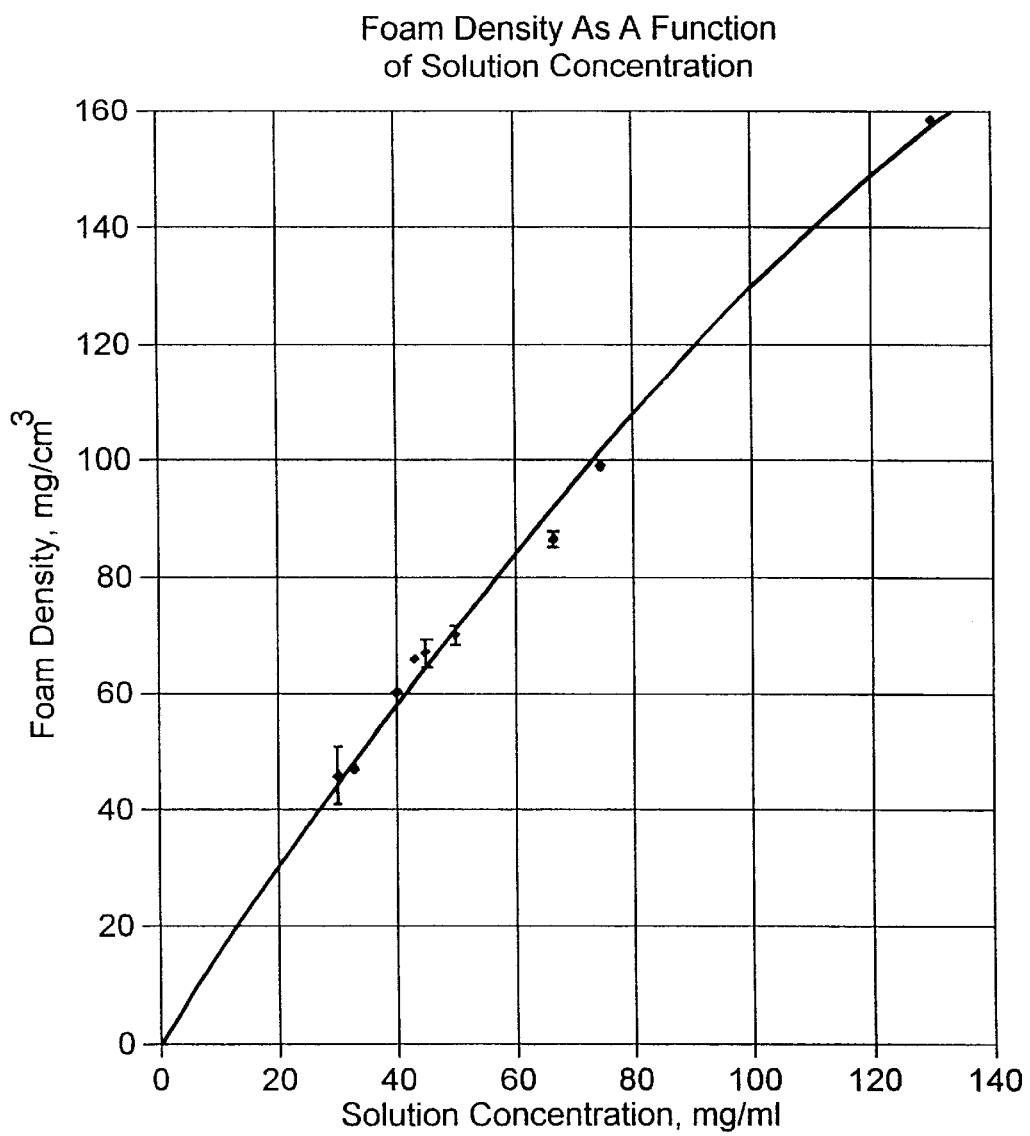
FIG. 2 is a graph showing the density of the biopolymer matrix foam coating as a function of the concentration of the preparation colution.
Figure 3A:
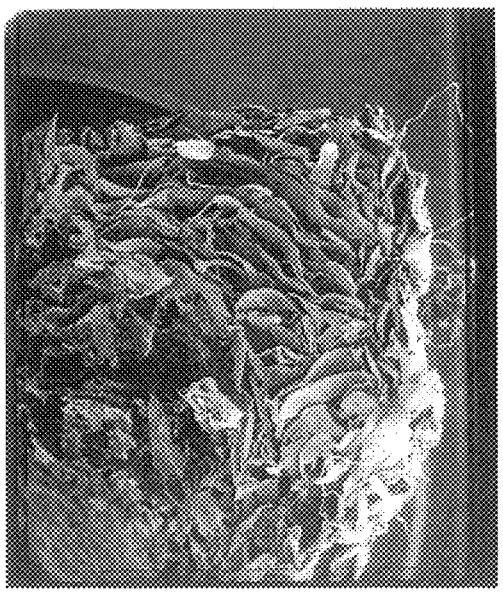
FIGS. 3A–3D are scanning electron micrographs showing the structure of the biopolymer matrix foam coating at magnifications of 20×, 100×, 100×, and 500×, respectively.
Figure 3B:
Figure 3C:
Figure 3D:
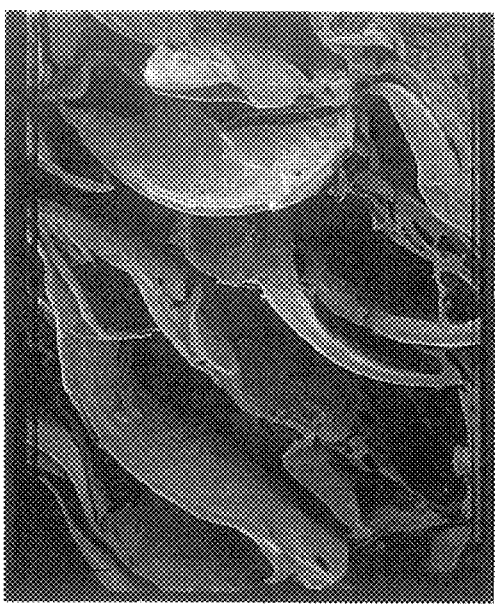

The incorporation of a bone graft is known to require cooperative interactions between the recipient site and the graft, each of which provides unique and indispensable contributions[17,34,37,63]. The graft provides a number of osteoinductive growth factors, such as the TGF-β-like bone morphogenetic proteins (BMP) and other non-collagenous proteins present in the matrix[2,108,115,152,157,162,163,165], and an osteoconductive structure that supports new bone formation in the host. The host bed provides an inflammatory response which results in a fibrovascular stroma that will eventually revascularize the graft and provide a source for the recruitment and transformation of mesenchymal cells into osteogenic and chondrogenic cells[17].

The sequence of histological events in the incorporation of massive, non-vascularized, segmental bone allografts has been extensively described in animals[13,14,16,18,151,153]. A hematoma is initially formed, which is the origin of platelet derived growth factors, other growth factors and cytokines. A local inflammatory response is usually stimulated by the implantation procedures and by the presence of the graft[13,14]. The formation of the fibrovascular stroma occurs within days. The connective tissue surrounding the graft conveys recipient-derived blood vessels and osteogenic precursors to the graft[35]. The invasion of vascular buds into cortical bone usually occurs through pre-existing Haversian or Volkman channels[35]. These channels are widened by osteoclastic activity that accompanies the neo-vascular response. Osteoclastic resorption of the bone allograft commonly occurs from the periosteal surface and at the junction with the host bone. In fresh frozen cortical bone allografts, this resorption may penetrate only a few millimeter into the graft[103,106].

After the initiation of graft resorption with following revascularization, new bone formation begins. These two concurrent processes may result in an adaptive remodeling response of the graft to biomechanical loading[144,153]. From a clinical standpoint, a graft has been successfully incorporated when the host-graft interface unites and the host-graft bone construct tolerates physiological weight-bearing without fracture or pain. From a basic science perspective, a bone allograft is successfully incorporated when the original graft bone has been completely substituted with new host bone. The incorporation of bone allografts can, therefore, be defined as the concurrent revascularization and substitution of non-viable allogeneic graft bone with viable autologous host bone without substantial loss of strength. The resulting composite of graft and host bone can bear physiological loads and can repair and remodel itself in response to changes in load or fatigue damage[143]. Experimental data suggest that the inflammatory response observed during the first one to three weeks is most likely to be the result of wound healing and a non-specific foreign body response[13-16]. While in autologous bone grafts these processes resolve in the direction of angiogenesis and osteogenesis with revascularization and new bone formation, the inflammatory response commonly persists in bone allografts resulting in continuous resorption. Because large segmental bone allografts present a depot of antigens, the ongoing resorption may provide a slow but steady release of antigens over a long period of time[17,36,38,63]. This could facilitate a persisting exposure of more antigens resulting in a chronic immune response. Interference with the initiation of the remodeling cycle due to impairment of osteoinductive processes and revascularization from the surrounding fibrovascular stroma is possible.

The major complications of massive cortical bone allografts (fractures, non-union, and infection) have been the subject of, or included in, several reviews. These studies have presented evidence that the causes of these complications are still poorly understood. However, many investigators hypothesized that at least some of these complications are immunologically mediated[33,38,39,49,53,64,117,118,143,161]. It appears likely that antigens carried by the bone allograft stimulate a specific immune response that activates immune competent cells in the host. In clinical studies, this response has been observed to develop as early as one month after surgery[33,41,116,147,154]. These cells secrete cytokines such as interleukin 1, tumor necrosis factor alpha and beta, which are also known as potent activators of the osteoclastic cell lineage and therefore may stimulate accelerated bone resorption[6,54,55,128,160,167,168]. Since bone resorption must occur before new bone can be formed, a delicate balance between the two concurrent processes must be maintained for the graft to be revascularized and substituted by host bone without appreciable loss of strength. A link between the presence of a chronic immune response and an accelerated resorption with premature mechanical failure of the bone allograft may exist, but no definite data is available indicating that these events are of any significance for the development of clinical complications. However, bone allografts are an excellent antigenic source and are capable of stimulating an immune response in the host.

Therefore, bone allografts generally appear to be subject to many of the same principles of transplantation as any other parenchymal organ transplant. However, bone allografts present with a number of tissue related characteristics which make the identification of a rejection more difficult. In comparison to parenchymal organs, such as kidneys, in which there are readily identifiable markers of function, no systemic marker exists which would allow quantifying the rejection of an allogeneic bone transplant. Biopsies and techniques, such as bronchial alveolar lavage in lung transplants, allow a very specific diagnosis of rejection. However, biopsies are difficult to evaluate in allogeneic bone transplants because the cellular infiltrate is generally not uniform. In addition, it is often difficult to obtain biopsy specimens or the transplant is not expendable[30]. The definition of bone allograft rejection is therefore usually inferred from resorption of the bone graft, premature mechanical failure, due to fatigue and the lack of incorporation of the graft into host bone.

The effect of histocompatibility matching on the incorporation of bone allografts has been investigated in controlled animal studies[9,10,52,64,141,142,144]. Humoral and antibody-dependent cell-mediated cytotoxicity were affected by matching with tissue antigens more than the cell-mediated immunity. The incorporation of canine non-vascularized bone allografts was enhanced by matching for tissue antigens. The magnitude of the immune response appeared to be modulated by the degree of tissue antigen matching[141,142,144]. The volume of fibrous connective tissue within the intratrabecular spaces was found to be directly proportional to the antigenicity of the graft. The percentage of osseous surface that was undergoing remodeling tended to be inversely proportional to the immunogenicity of the graft[144]. These data from an experimental animal model must be interpreted cautiously, and direct extrapolations to the clinical outcome maybe inappropriate. Cumulative observations suggest that major histocompatibility complex (MHC) mismatches may have a deleterious influence particularly on the fate of massive osteochondral allografts.

The influence of immune responses on these large grafts in humans is unclear. Small fresh, frozen[83,84] and freeze-dried[41,135] grafts have been shown to elicit cellular and humoral immune responses, but these did not appear to affect incorporation. In studies on large grafts, 85% of recipients of bone allografts were found to have an antibody response when tested against a cell panel[131], but an almost identical number was found in a control population, possibly as a result of receiving transfusions or having been pregnant[131]. Two other studies have failed to establish a clear correlation between the degree of donor/recipient histocompatibility and clinical complications[88,94,116,147,148]. Their incidence is therefore probably more related to a delay in incorporation, which, at least in part, may be mediated through the immune system.

It is, however, important to note that these complications are multifactorial in origin and that the effect of factors such as fit of the graft, internal fixation device application, mechanics of the extremity, vascularity of the tissue bed, and the use of adjuvant radiation or chemotherapy must be included in any assessment of the response of the grafts to the immune reaction of the host. Studies to date have failed to provide satisfactory definition of the relationship of immune responses and the results of bone allograft transplantation in humans, in part due to their lack of consideration of these variables.

Previous studies have attempted to improve host incorporation by altering the geometrical surface configuration of cortical bone[3,45,46,122,133,137]. The mechanism by which such alterations promoted osteogenesis and incorporation include the following possibilities: The greater surface area of the bone graft or improved access to vascular tissue, or a combination of the two factors. Previous studies have pointed out that the geometry of an implant may influence the extent of bone formation. As such, the osteoconductive potential of cortical bone allografts treated in such a way has been attributed, at least in part, to its morphometric similarity to cancellous bone, which is highly osteoinductive.

Demineralization has been extensively studied in an attempt to foster new bone formation in bone allografts. This approach is known to result in the exposure of osteoinductive non-collagenous bone matrix factors[166] such as TGF-β bone morphogenetic proteins (BMP)[20,21,157,163-166] and sialoproteins including osteopontin[22], bone gla protein[28] osteocalcin[59,61,97,110] and others to the surrounding soft tissues. These factors contribute to the transformation of mesenchymal cells into osteogenic and chondrogenic cells[50] required for induction of bone resorption and formation of new bone[51]. In addition, acid demineralization is thought to lead to depletion of cellular components within the graft that express transplantation antigens[158]. Since there is sufficient evidence for both antibody mediated and cellular mediated cytotoxicity from in vivo and in vitro experiments with bone allografts[11,25,34,40,73,83,120,123,136], which have indicated that the primary response of the host to the bone allograft is predominately a cellular mediated response to the MHC encoded cell surface antigens carried by cells within the allograft and recognized by responding T-lymphocytes in the host[10,40,83,118,140], the effect of demineralization on graft incorporation may therefore potentially be two-fold. It should improve osteoinduction and reduce graft rejection.

Gendler used fully demineralized diaphyseal allogeneic struts that were perforated with the use of a mechanical drill[45]. In comparison, O'Donnell et al. used demineralized calvarial cortical bone[122]. Bernick et al. characterized the inductive cellular events in a similar system[3]. Scanlon implanted demineralized canine femoral strut allografts in orthotopic model[133]. The later two studies have demonstrated the use of an Erbium:Yttrium-Scandium-Gallium-Garnet (Er:YSGG) laser for drilling of cortical bone allografts, thereby increasing the porosity and allowing demineralization to proceed to areas that would normally be inaccessible to the demineralization process. When reimplanted, these grafts may therefore be more osteogenic than cortical grafts without holes. The effect of drill holes and partial demineralization may therefore rely on the modification of cortical bone allografts into a more porous scaffold, facilitating the development of focal centers of bone resorption and new bone formation. If the net result of this incorporation process is in favor of new bone formation, the graft will eventually be fully replaced by the recipients own bone.

Studies by the inventors have indicated that osteogenesis in orthotopically transplanted cortical bone grafts could be fostered through the process of partial demineralization and laser ablation[87,92,93]. To the extent that minimal partial demineralization and laser ablation may allow maintenance of structural integrity while altering the osteoinductive properties in such a way as to promote ingrowth of new bone, this experimental model represented an advance in understanding how osteogenesis in cortical bone grafts could be improved. A large-scale animal study using sheep confirmed the improved incorporation of controlled partial demineralization and laser-drilling for enhancement of incorporation of large bone allografts.

However, problems such as accelerated graft resorption with bone loss were present[89-91]. These observations were likely due to donor-specific immune responses because substantial bone loss occurred in mismatched donor-recipient pairs. Results of the sheep study showed that development of donor-specific alloantibodies is minimized by the demineralization process but not eliminated, as assessed by crossmatching donor T-cells with recipient serum obtained at various postoperative intervals[89]. Differences in the tissue type of donor and recipient animals were evaluated by one-dimensional isoelectric focusing of class I molecules[78,79,129]. Mismatches were assessed by running samples of donor and recipients in parallel and comparison of specific bands. Mismatches were related to presence of allostimulation. Of the donor-recipient pairs with a mismatch in the transplantation antigens, all recipients stimulated an immune response where the bone allografts which underwent excessive bone resorption. In laser-perforated and partially demineralized bone allografts, donor specific alloantibodies, if present after transplantation, were undetectable after the grafts were completely incorporated. This suggested that antigens of the graft were more effectively presented and processed when allografts were undergoing accelerated resorption.

The preceding observation is consistent with clinical data from a previous historical clinical control group, whose patients received fresh frozen bone allografts. It also supports the hypothesis that immune responses to allograft transplantation of cortical bone may not result in immediate graft failure but, rather, may set the stage for chronic rejection with continuous bone resorption.

Since the grafts used in the previously described, large-scale sheep study, were comparable to a large skeletal defect often seen in the clinical situation of bone tumor resection, the inventors hypothesized that protection of large cortical bone allografts from the host's immune system, by application of a surface coating that the graft recipient will recognize as "self", will enhance graft survival and, therefore, result in better clinical outcome.

This hypothesis is further substantiated by a previous immunological study conducted by the inventors, in which the presence of cytotoxic antibodies was detected in sixteen patients who received eighteen large frozen bone allografts[148]. Donor-specific antigens were identified by testing recipient sera against donor T cells in a crossmatch test and by testing reactivity of serum against a cell panel of 38 different class I determinants. HLA class I mismatches were evaluated by tissue typing donors and recipients. Results suggested that large frozen bone allografts frequently evoke a humoral immune response with antibody-dependent cytotoxicity in their host.

All patients with a positive crossmatch developed donor specific cytotoxic alloantibodies against public and private domains of the MHC class I molecule encoded by the HLA-A, HLA-B, and HLA-C locus. Cell-mediated immunity was evaluated with the use of a cell-free ELISA for the serum levels of the soluble portion of the interleukin 2 receptor (IL2R). This assay was run simultaneously with the crossmatches, utilizing sera previously obtained from recipients. Although half of the patients with an immune response had clinical complications, no direct correlation between antibody-dependent and cell-mediated cytotoxicity and clinical outcome could be established. The cumulative evidence from both the experimental study in sheep[89] and the historical clinical study[88,148] suggested that immune response of recipients to their bone allografts may influence their clinical outcomes.

The present invention solves this problem and achieves protection of the graft by surface coating the graft substrate with the recipient's own periosteal cells (autologous cells). Specifically, the invention relates to a method by which immune responses to the graft substrate material, e.g., cadaver cortical bone, can be minimized and at the same time the osteoinductive potential of the graft can be improved. Other substrate materials such as a resorbable precured bone cement, a molecularly reinforced interpenetrating network and a molded bioerodible polymer are also contemplated. Furthermore, the invention provides new types of bone grafts that heal better and more rapidly with the host bone, eliminating long-term complications, such as fracture, non-union, infection, and rejection. The composite biocompatible bone grafts of the invention are modified to have an osteoinductive surface that the graft recipient's body will recognize as its own tissue type and, therefore, will not reject. The osteoinductive surface modification comprises a porous biopolymer coating that is seeded with periosteal cells that have been previously harvested from the graft recipient.

The present invention provides novel and unique surface characteristics in a new type of bone graft that will help to develop immunologic tolerance in the recipient towards the graft. Development of immunologic tolerance of the transplant will result in accelerated incorporation and in improved clinical outcomes. As such, the use of periosteal cells from the recipient of the bone graft represents a new approach.

The advantage of the materials and methods of the invention over former bone grafting techniques include minimal tissue damage to the graft as the need for further processing is eliminated. Use of the recipient's own periosteal cells will result in rapid formation of a periosteal bone cuff surrounding the bone graft. This periosteal bone cuff will not only protect the graft from the recipient's immune system but also promote its incorporation, by increased osteogenesis and accelerated direct bone formation.

The following examples are presented to illustrate the advantages of the present invention and to assist one of ordinary skill in making and using the same. These examples are not intended in any way otherwise to limit the scope of the disclosure.

EXAMPLE I

Preparation of Graft Substrate Material

The graft substrate material can be any rigid, biocompatible substrate that can be prepared or formed into a suitable shape. In one embodiment, the graft substrate is a bone section from a donor, e.g., from a cadaver, which is stripped of soft tissue and periosteum and from which the marrow is removed under pressure with saline.

Another possible graft substrate material is a resorbable precured bone cement. Such a bone cement comprises a hydrolyzable biopolymer containing carbon-carbon unsaturation, such as poly(propylene fumarate) (PPF), which enables the biopolymer to undergo crosslinking with a suitable crosslinking reagent; a crosslinking agent, comprising a vinyl monomer such as N-vinyl-2-pyrrolidone; an initiator to induce crosslinking such as benzoyl peroxide; an inorganic filler of limited solubility which may serve to increase the strength of the cured cement, and may also promote healing; such as hydroxyapatite (also known as hydroxyl apatite) a calcium mineral closely resembling the inorganic component of bone and which is also known to be osteoconductive; a relatively soluble biocompatible material, preferably a calcium salt of an organic acid, such as, but not limited to, calcium acetate, calcium propionate, or calcium gluconate or any combination of these, which will generate porosity in the presence of tissue fluids by dissolution and diffusion from the implant site; optional accelerators and inhibitors, included to control the cure rate; and other optional components, including reinforcing aids such as fibers to further strengthen the device.

Following compounding according to the above formulation, the bone cement may be cured ex vivo to a bone-like hardness in molds that, in shape, approximate the bone segment to be replaced. Alternatively, the bone cement may be machined after curing to the desired shape.

In addition, a molecularly reinforced interpenetrating network can be useful as the allograft substrate material. In this embodiment, the substrate is a resorbable composite comprising two resorbable, hydrolyzable biopolymers, one of which contains carbon-carbon unsaturation enabling it to be crosslinked in the presence of the other to form a molecularly reinforced inpenetrating network. This material to comprises a hydrolyzable biopolymer containing carbon-carbon unsaturation, such as poly(propylene fumarate) (PPF), which enables the biopolymer to undergo crosslinking with a suitable crosslinking reagent; a hydrolyzable biopolymer such as poly(lactide-co-glycolide), preferably with a lactide:glycolide ratio of 70:30 to 90:10; a crosslinking agent which may be a vinyl monomer such as N-vinyl-2-pyrrolidone (VP); an initiator such as benzoyl peroxide; and, optionally, accelerators such as N,N-dimethyl-p-toluidine and inhibitors such as hydroquinone.

The polymers may first be dissolved in a mixture of a low boiling solvent such as acetone and the crosslinking agent VP, after which the solvent may be removed by controlled evaporation, leaving the high boiling VP in the polymer mixture. This plastic material is compression molded and the mold heated to effect cure. After curing, it may be in its final shape or may require machining. Alternatively the two polymers may be dissolved in the crosslinking agent directly without the use of a low boiling solvent.

The allograft substrate material may also, suitably, be a molded bioerodible polymer, such as poly(lactide-co-glycolide) X:Y (PLGA), where X:Y is the mole ratio of lactide to glycolide moieties comprising the PLGA. The lactide moiety of the PLGA bone substitute may be d,l-lactide or l-lactide and the X:Y ratio may vary from 0:100, i.e., poly(glycolide), to 100:1, i.e., poly(d,l-lactide), or poly(l-lactide). The PLGA may then be molded to the desired shape, and machined if required, to its final form before coating.

EXAMPLE II

Coating of the Allograft Substrate with a Polymer Foam

The surface of the cured material or graft substrate may be roughened to secure better attachment of the foam. Roughening may be accomplished by mechanical means such as grinding or sanding. Alternativley, holes of less than 1 mm dia and spaced about 5 mm apart both axially and radially may be drilled radially through the bone or for some distance into the bone. The substrate may also be exposed to laser pulses for altering the surface topography. An Er:YAG laser may also be used for drilling holes either partially through or completely through the substrate in order to secure better attachment of the foam.

The additional use of laser drilling and partial demineralization in combination with tissue-engineered surface modifications should further enhance incorporation for two reasons. The demineralized bone matrix surrounding the bone allograft should provide a highly osteoinductive matrix for the ingrowth of periosteal cells from the foam into the allograft. Second, it may release growth factors from the demineralized bone matrix stimulating the expansion of periosteal cells from the foam into the graft. Thus, further processing of cortical bone allografts by employing a tissue-engineered surface modification is consistent with previous attempts at enhancing their incorporation into host bone.

Previous studies have attempted to improve host incorporation by altering the geometrical surface configuration of cortical bone[3,45,46,122,133,137]. The mechanism by which the presence of laser holes promoted osteogenesis and incorporation in partially demineralized grafts include the following possibilities: the greater surface area of partially demineralized bone or increased access to vascular tissue, or a combination of the two factors. Previous studies have pointed out that the geometry of an implant may influence the extent of bone formation. As such, the osteoconductive potential of cortical bone allografts treated in such a way has been attributed, at least in part, to its morphometric similarity to cancellous bone. In addition, demineralization alone would yield a geometrical surface configuration that is less advantageous for bony ingrowth when compared with cancellous bone because cortical bone is less porous and has a comparatively low surface area to volume ratio. The effect of drill holes and partial demineralization may, therefore, rely on the modification of cortical bone allografts into a more porous scaffold facilitating the development of focal centers of bone resorption and new bone formation.

If desired, the graft may be partially demineralized before or after roughening by incubation in dilute hydrochloric acid at room temperature. This treatment produces a demineralization to a depth proportional to the duration of the treatment. After treatment, the bones are washed with phosphate buffered saline (PBS) to remove the acid. PBS under pressure is used to remove the marrow. The approach of using hydrochloric acid demineralization for surface modification was chosen because it is known to result in the exposure of osteoinductive non-collagenous bone matrix factors[166] such as TGF-β bone morphogenetic proteins (BMP)[21,22,157,163-165] and sialoproteins including osteopontin[22], bone gla protein[28], osteocalcin[59,61,97,110], and others to the surrounding soft tissues. These factors contribute to the transformation of mesenchymal cells into osteogenic and chondrogenic cells[22] required for induction of bone resorption and formation of new bone[51]. Surface decalcification of cortical bone allografts has been shown to enhance their incorporation but problems such as bone resorption in excess of the rate of new bone formation and immune responses persisted.

There is sufficient evidence for both antibody-mediated and cellular-mediated cytotoxicity from in vivo and in vitro experiments with bone allografts[10,25,33,34,73,83,120,123,136]. These studies have indicated that the primary response of the host to the bone allograft is predominately a cellular-mediated response to the MHC encoded cell surface antigens that are carried by cells within the allograft and recognized by responding T-lymphocytes in the host. The use of demineralization for processing of bone allograft may have a twofold effect. It should improve incorporation by enhancing their osteoinductive potential. In addition, it should reduce immunogenicity of the graft because irrigation of the graft with solutions such as hydrochloric acid, Triton X or other defattening solutions has been shown to reduce the cellular antigen load within the graft.

The polymer foam is prepared by dissolving the dried biocompatible polymer material, e.g., PLGA, preferably poly(d,l-lactide-co-glycolide)-50:50, in a suitable solvent, preferably glacial acetic acid. As can be seen in FIG. 1, high lactic acid content adversely affected cell seeding; specifically, fewer than half the number of cells attached to a 75%PLA/25%PGA scaffold than attached to a 0%PLA/100% PGA scaffold. This suggests that minimizing the lactic acid content would optimize the cell seeding process and maximize the osteogenic potential of the constructs. On the basis of these cumulative data, it appears reasonable to manufacture the foam cuff from PLGA 50:50. This formulation would be suitable from a polymer-engineering perspective because, as well as having high seeding efficiency, it will degrade somewhat more slowly, a desirable property because the high surface area presented by the foam will facilitate more rapid hydrolytic degradation.

The solution concentration determines both the density and pore size distribution of the final foam coating, as shown in Table 1. The consequences of changing pore size has a major impact on surface availability for periosteal cell activity. Porosity, pore size and pore structure are important factors that are associated with nutrient supply to transplanted and regenerated cells. Small-diameter pores are preferable, to yield high surface-area-to-volume ratios, as long as the pore size is greater than the diameter of a cell in suspension. In the case of bone regeneration, there is an optimal pore size for maximum tissue ingrowth, ranging from about 200 to about 400 μm (BOYAN et al., 1996). Knowledge of both growth factor and cell transport into the foam matrix is necessary for the optimization of the geometry of the foam cuff. When seeding the surface of an ideal porous medium, the drop in cell number is expected to be logarithmic with depth, suggesting that the bulk of the periosteal cells may be confined within the first few hundred micrometers depth of the foam cuff (CATTANEO et al., 1997).

The chosen graft substrate is then evenly coated with the polymer solution. This may be accomplished either by dipping the substrate into the solution or by brushing the solution onto the substrate. Other methods may also be employed, such as spray-coating the solution onto the substrate. The advantage of dip-coating is that the solution may be forced into the pores or interstices formed by the roughening or drilling procedures, by rapid application and release of vacuum.

Once the substrate is coated completely, it is removed from the solution and placed in a chilled lyophilization flask which is placed in a freezer until the polymer solution layer is frozen. The coated bone is then lyophilized to remove the solvent, e.g., glacial acetic acid, leaving the PLGA in the form of a open-celled foam layer on the substrate.

The thickness of the PLGA coating may be 0.5 to 2.5 mm, depending on the solution concentration and thickness of the liquid layer adhering to the substrate on removal from the polymer solution. A preferred thickness is approximately 1.0 to 2.0 mm.

TABLE 1

PLGA Foam Density as a Function of PLGA Concentration in Glacial Acetic Acid Solution

| Solution Conc., mg/ml | Foam Density, mg/cm$^3$ | Solution Conc. mg/ml | Foam Density, mg/cm$^3$ |
|---|---|---|---|
| 30.0 | 46.3 ± 4.9 | 50.0 | 70.5 ± 1.7 |
| 32.8 | 47.2 | 66.7 | 86.7 ± 1.1 |
| 40.0 | 61.0 | 74.7 | 98.0 |
| 42.9 | 66.3 | 130.0 | 158.0 |
| 45.0 | 67.3 ± 2.3 | | |

The structure of the polymer coating is that of an open celled foam with a leaflet or platelet-like structure. This structure is shown in the scanning electron micrographs of FIGS. 3A–3D, which are at a magnification of 20×, 100×, 100×, and 500×, respectively.

The approach of using a bioresorbable foam having an open window structure as a carrier for tissue engineered surface modification, stems from the fact that bone has a considerable potential for regeneration. In fact, it is considered by some to be the prototypic model for tissue engineering (LAURENCIN 1996, REDDI 1998). Development of composites of extracellular matrix and stem cells responding to regulatory signals has been at the center of engineering skeletal tissues and is the main goal of this proposal. In fact, leading strategies on engineering and regeneration of skeletal tissues are largely based on observations of local bone induction after implantation of demineralized bone matrix into subcutaneous sites. These models have allowed to study sequential limb morphogenesis and has permitted the isolation of bone morphogens, such as bone morphogenetic proteins (BMPs), from demineralized adult bone matrix. BMPs initiate, promote, and maintain chondrogenesis and osteogenesis. Therefore, it appears reasonable to approach our biodegradable foam as a scaffold that will function as a cell and tissue carrier, emphasizing material superstructuring in the design of surface-modified and tissue-engineered cortical bone allografts. Therefore, a biodegradable superstructure that will provide optimal spatial and nutritional conditions for cell maintenance, by the arrangement of structural elements (e.g., pores or fibers) so as to vary the order of cell-to-cell contact (WINTERMANTEL 1996) is engineered. For example, 3-dimensional cell-polymer matrices for tissue engineering are needed that allow osteoblast cells to maintain their phenotypic properties and to form a mineralized matrix while seeded on the polymer surface (PUELACHER 1996, RIVARD 1996).

EXAMPLE III

Periosteal Cell Culture Model System

The approach of using recipient periosteal cells stems from the observation that these cells can be readily cultured from periosteal tissue (KOSHIHARA et al., 1989; NAKAHARA et al., 1990). In addition, they grow extremely well in synthetic polymeric, as well as in natural collagenous, matrices and are therefore recognized as an extremely osteoinductive material (UCHIDA et al., 1988). Paralleling attempts to take dermal fibroblasts for the in vitro expansion of autologous articular cartilage cells (BRITTBERG 1994), it is logical to take periosteal cells from the future recipient of bone allograft and to expand them in vitro for tissue engineering purposes. Breitbart et al. (1998) have already demonstrated the feasibility of the use of periosteal cells for tissue-engineered bone repair of calvarial defects. In analogy, a new type of tissue-engineered bone allograft, using periosteal cells of the future recipient, should show improved enhanced incorporation and significantly lower sensitization rates. Both antibody-mediated immunity and cellular-mediated cytotoxicity should be reduced simply by the formation of a dense autologous periosteal bone cuff surrounding the bone transplant.

The feasibility of such a tissue-engineering approach depends on the ability to obtain a population of cells which have or will develop osteoblast-like function. For the purpose of this study, the source of cells was chosen to be long bone periosteum, due to: 1) its relatively easy surgical accessibility; and 2) the known osteogenic properties of its cells. The periosteum itself is known to play a critical role in fracture healing and callus formation (UTVAG 1996, ARO 1990), which is presumably cell-mediated. Cells derived from periosteum are capable of forming bone in subcutaneous sites either alone (NAKAHARA 1991), or when seeded onto ceramic calcium phosphate (NAKAHARA 1992) or onto polymeric PGA (KIM 1995) substrates. Further, the healing of critical size defects in the cranium (VACANTI 1995) and femur (PUELACHER 1996, BREITBART 1998) have been demonstrated, using periosteal cells seeded onto PGA scaffolds. Cells from the periosteum are known to have both osteogenic (NAKAHARA 1991) and chondrogenic (RUBAK 1982) potential, and the process of bone formation from periosteal cells involves transition through a cartilage-like phase (KIM 1995). Studies examining the use of chondrocytes on polymer scaffolds to fill bone defects have demonstrated the formation of stable cartilage that does not generate bone (KIM 1994). Periosteal cells placed in the same material in the same site ultimately repair the defect with bone (VACANTI 1994). With this in mind, coating cryopreserved bone with PLGA foam, followed by seeding with periosteal cells, appears to be an optimal process. This process takes advantage of the initial strength and geometry of the allograft, while accelerating the resorption of the transplanted bone and minimizing the immune response to foreign tissue.

Intact tibias from inbred male Sprague Dawley rats were obtained and used to develop a periosteal cell culture model system. Under sterile conditions, the periosteum was excised and cut into 2 mm×2 mm pieces. Individual pieces were placed into 6-well culture plates for 10–20 minutes to facilitate attachment to plastic, and washed twice with phosphate buffered saline (PBS) containing antibiotics. Alternatively, pieces of periosteum may be placed directly on top of PLGA scaffolds to induce attachment of the tissue to the polymer, and the tissue/polymer constructs may then be placed into 6-well culture dishes and washed twice with antibiotics, e.g., penicillin at 10000 U/mL and streptomycin at 10 mg/mL. Subsequently, periosteal samples, in dishes or tissue/polymer constructs, were covered with 3 ml Medium 199 containing 10% FBS, 20 mg/ml ascorbate, and antibiotics. Migration of cells from periosteal samples is monitored daily, and fresh medium added every 3 days. Migration of cells out of periosteum samples is stopped when 60–80% confluence is reached. Cells are removed from plates with 0.05% trypsin and 0.53 mM $Na_2EDTA$ and either replated at a density of 2,500 cells/$cm^2$ or seeded onto polymer scaffolds. This will allow the production of sufficient material for seeding the foam coating of bone graft substrates.

EXAMPLE IV

Animal Transplantation Studies

Adult male Sprague Dawley rats are used as a recipient animal model system. Bone grafts consist of eight-mm-long diaphyseal segments, which are excised from the midportion of tibias obtained from Wistar donor rats. The grafts are stripped of attached soft tissues, including the periosteum. The marrow is removed by repeated washings with saline. Grafts are stored at −80° C. until use. As described above, grafts are coated with polymer and then seeded with periosteal cells. Using a model established by the inventors[92,93], grafts are implanted orthotopically by removing an eight-mm-long diaphyseal segment from the tibia and implanting one of the experimental grafts. The periosteum from the host bed is removed and the bone marrow from the ends of the host bone is washed out. Fixation is achieved with a 0.062" threaded K-wire as an intramedullary rod. Animals are sacrificed at four or sixteen weeks postoperatively and used for mechanical testing or histological analysis of the grafts. Grafts are evaluated by high resolution radiography, dual-energy x-ray absorptiometry (DXA), histology and histomorphometry.

Figure 4A:
FIGS. 4A and 4B are photomicrographs of longitudinal sections of rat tibia into which activated biopolymer foam scaffolding of the invention has been injected.
Figure 4B:

To demonstrate the suitability of the bioresorable PLGA-based foam for bony ingrowth prior to its use for periosteal cell seeding, an initial in vivo biocompatibility study in rats was conducted using the tibial defect model of Gerhart et al. The PLGA-based foam (PLGA 85:15) was injected with use of an 18G needle into a tibial defect (a drill hole measuring 1 mm in diameter) created in male Sprague-Dawley rats (Charles River Breeding Laboratories) weighing approximately 200 grams. The foam-injected group was compared to a sham-operated group having a drill hole but no implant. Groups of 8 animals were sacrificed at 1, 3, 5, and 7 weeks postoperatively. Thus, a total of 64 rats was operated on, in 8 groups. Hemoxylin and eosin sections of all specimens were examined microscopically for determination of early-stage bicompatiblity. Histologic evaluation of these sections showed new woven bone formation in animals injected with the PLGA-based foam, as early as one week postoperatively (see photomicrographs, FIGS. 4a and 4b). FIG. 4a shows that the drill hole in a rat tibia injected with 85:15-PLGA-based foam, was completely filled with newly formed, woven bone. FIG. 4B shows remnants of the PLGA-based foam, between the trabeculae of the newly formed woven bone, undergoing active resorption.

These results demonstrated that the bioresorbable PLGA-based foam is capable of serving as a scaffold for bone ingrowth and is suitable for seeding with periosteal cells. The bone that grew in the foam scaffold most likely stemmed from the periosteum adjacent to the drill hole and grew into the hole "per continuum" by appositional growth.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. AATB: Standards for tissue banking. McLean, V A, American Association of Tissue Banks, 1991.
2. AIDINGER, G.; HERR, G.; KUSSWETFER, W.; REIS, H. J.; THIELEMANN, F. W.; AND HOLZ, U. Bone morphogenetic protein: a review. Int. Orthop. 15: 169–177, 1991.
3. BERNICK, S.; PAULE, W.; ERTL, D.; NISHIMOTO, S. K.; AND NIMNI, M. E. Cellular events associated with the induction of bone by demineralized bone. J. Orthop. Res. 7: 1–11, 1989.
4. BERREY, B. H., JR.; LORD, C. F.; GEBHARDT, M. C.; AND MANKIN, H. J. Fractures of allografts. Frequency, treatment, and end-results. J. Bone Joint Surg Am. 72: 825–833, 1990.
5. BERREY, B. H. J.; LORD, C. F.; GEBHARDT, M. C.; AND MANKIN, H. J. Fractures of allografts. Frequency, treatment, and end-results. J. Bone Joint Surg. Am. 72: 825–833, 1990.
6. BERTOLINI, D. R.; NEDWIN, G. E.; BRINGMAN, T. S.; SMITH, D. D.; AND MUNDY, G. R. Stimulation of bone resorption and inhibition of bone formation in vitro by human tumour necrosis factors. Nature, 319: 516–518, 1986.
7. BIRKEDAL-HANSEN, H. Kinetics of acid demineralization in histologic technique. Journal of Histochemistry & Cytochemistry, 22: 434–441, 1974.
8. BIRKEDAL-HANSEN, H. Kinetics of acid *demineralization* in histologic technique. Journal of Histochemistry & Cytochemistry, 22: 434–441, 1974.
9. BOS, G. D.; GOLDBERG, V. M.; GORDON, N. H.; DOLLINGER, B. M.; ZIKA, J. M.; POWELL, A. E.; AND HEIPLE, K. G. The long-term fate of fresh and frozen orthotopic bone allografts in genetically defined rats. Clin. Orthop. 245–254, 1985.
10. BOS, G. D.; GOLDBERG, V. M.; POWELL, A. E.; HEIPLE, K. G.; AND ZIKA, J. M. The effect of histocompatibility matching on canine frozen bone allografts. J. Bone Joint Surg. Am. 65: 89–96, 1983.
11. BOS, G. D.; GOLDBERG, V. M.; ZIKA, J. M.; HEIPLE, K. G.; AND POWELL, A. E. Immune responses of rats to frozen bone allografts. J. Bone Joint Surg. Am. 65: 239–246, 1983.
12. BUCKLEY, P. D.; GEAREN, P. F.; AND PETTY, R. W. Structural bone-grafting for early atraumatic avascular necrosis of the femoral head. J. Bone Joint Surg. Am. 73: 1357–1364, 1991.
13. BURCHARDT, H. The biology of bone graft repair. Clin. Orthop. 28–42, 1983.

14. BURCHARDT, H. Biology of bone transplantation. Orthop. Clin. North Am. 18: 187–196, 1987.
15. BURCHARDT, H. AND ENNEKING, W. F. Transplantation of bone. Surg. Clin. North Am. 58: 403–427, 1978.
16. BURWELL, R. G. Studies in the transplantation of bone. V. The capacity of fresh and treated homografts of bone to evoke transplantation immunity. J. Bone Joint Surg. [Br]. 45: 386401, 1963.
17. BURWELL, R. G.; FRIEDLAENDER, G. E.; AND MANKIN, H. J. Current perspectives and future directions: the 1983 Invitational Conference on Osteochondral Allografts. Clin. Orthop. 141–157, 1985.
18. BURWELL, R. G. AND GOWLAND, G. Studies in the transplantation of bone. III. The immune responses of lymph nodes draining components of fresh homologous cacellous bone and homologous bone treated by different methods. J. Bone Joint Surg. [Br]. 41: 160–171, 1959.
19. CARA, J. A. AND CANADELL, J. Limb salvage for malignant bone tumors in young children. J. Pediatr. Orthop. 14: 112–118, 1994.
20. CELESTE, A. J.; IANNAZZI, J. A.; TAYLOR, R. C.; HEWICK, R. M.; ROSEN, V.; WANG, E. A.; AND WOZNEY, J. M. Identification of transforming growth factor beta family members present in bone-inductive protein purified from bovine bone. Proc. Natl. Acad. Sci. U. S. A. 87: 9843–9847, 1990.
21. CENTRELLA, M.; HOROWITZ, M. C.; WOZNEY, J. M.; AND MCCARTHY, T. L. Transforming growth factor-beta gene family members and bone. [Review]. End. Rev. 15: 27–39, 1994.
22. CHEN, J.; SINGH, K.; MUKHERJEE, B. B.; AND SODEK, J. Developmental expression of osteopontin (OPN) mRNA in rat tissues: evidence for a role for OPN in bone formation and resorption. Matrix, 13: 113–123, 1993.
23. COLVIN, R. B.; FULLER, T. C.; MACKEEN, L.; KUNG, P. C.; IP, S. H.; AND COSIMI, A. B. Plasma interleukin 2 receptor levels in renal allograft recipients. Clin. Immunol. Immunopathol. 43: 273–276, 1987.
24. COLVIN, R. B.; PREFFER, F. I.; FULLER, T.; BROWN, M. C.; I P, S. H.; KUNG, P. C.; AND COSIMI, A. B. A critical analysis of serum and urine interleukin 2 receptor assays in renal allograft recipients. Transplantation, 48, No. 5: 800–804, 1989.
25. DAISAKU, H. Study on the immune response of mice receiving bone allografts. Nippon. Seikeigeka. Gakkai. Zasshi. 62: 71–83, 1988.
26. DAVIS, A.; BELL, R. S.; ALLAN, D. G.; LANGER, F.; CZITROM, A. A.; AND GROSS, A. E. [Fresh osteochondral transplants in the treatment of advanced giant cell tumors] Frische osteochondrale Transplantate in der Behandlung fortgeschrittener Riesenzelltumore. Orthopade. 22: 146–151, 1993.
27. DELMONICO, F. L.; FULLER, A.; COSIMI, A. B.; TOLKOFF RUBIN, N.; RUSSELL, P. S.; RODEY, G. E.; AND FULLER, T. C. New approaches to donor cross-matching and successful transplantation of highly sensitized patients. Transplantation, 36: 629–633, 1983.
28. DOHI, Y.; OHGUSHI, H.; TABATA, S.; YOSHIKAWA, T.; DOHI, K.; AND MORIYAMA, T. Osteogenesis associated with bone gla protein gene expression in diffusion chambers by bone marrow cells with demineralized bone matrix. J. Bone Miner. Res. 7: 1173–1180, 1992.
29. DUPREZ, V.; FERRER, M.; AND DAUTRY VARSAT, A. High-affinity interleukin 2 receptor alpha and beta chains are internalized and remain associated inside the cells after interleukin 2 endocytosis. J. Biol. Chem. 267: 18639–18643, 1992.
30. ELVES, M. W. AND FORD, C. H. A study of the humoral immune response to osteoarticular allografts in the sheep. Clin. Exp. Immunol. 17: 497–508, 1974.
31. ENNEKING, W. F. Limb salvage in Muscoloskeletal Oncology. In pp. 5Edited by W. F. Enneking. New York, Churchill Livingstone, 1987.
32. ENNEKING, W. F. AND MINDELL, E. R. Observations on massive retrieved human allografts. J. Bone Joint Surg. Am. 73: 1123–1142, 1991.
33. FRIEDLAENDER, G. E. The antigenicity of preserved allografts. Transplant. Proc. 8: 195–200, 1976.
34. FRIEDLAENDER, G. E. Immune responses to osteochondral allografts. Current knowledge and future directions. Clin. Orthop. 58–68, 1983.
35. FRIEDLAENDER, G. E. Bone grafts. The basic science rationale for clinical applications. J. Bone Joint Surg. Am. 69: 786–790, 1987.
36. FRIEDLAENDER, G. E. Current concepts review. Bone grafts. The basic science rationale for clinical application. J. Bone Joint Surg Am. 69: 786–790, 1987.
37. FRIEDLAENDER, G. E. Bone allografts: the biological consequences of immunological events [editorial]. J. Bone Joint Surg. Am. 73: 1119–1122, 1991.
38. FRIEDLAENDER, G. E. AND HOROWITZ, M. C. Immune responses to osteochondral allografts: nature and significance. Orthopedics. 15: 1171–1175, 1992.
39. FRIEDLAENDER, G. E.; SELL, K. W.; AND STRONG, D. M. Bone allograft antigenicity in an experimental model and in man. Acta Med. Pol. 19: 197–305, 1978.
40. FRIEDLAENDER, G. E.; STRONG, D. M.; AND SELL, K. W. Studies on the antigenicity of bone. I. Freeze-dried and deep-frozen bone allografts in rabbits. J. Bone Joint Surg. Am. 58: 854–858, 1976.
41. FRIEDLAENDER, G. E.; STRONG, D. M.; AND SELL, K. W. Studies on the antigenicity of bone. II. Donor-specific anti-HLA antibodies in human recipients of freeze-dried allografts. J. Bone Joint Surg. Am. 66: 107–112, 1984.
42. FLUKUHARA K.; SCHOLLMEIER G.; AND UHTHOFF H K. The pathogenesis of club foot. A histomorphometric and immunohistochemical study of fetuses. J. Bone Joint Surg. Br. 76: 450457, 1994.
43. GEBHARDT, M. C.; FLUGSTAD, D. I.; SPRINGFIELD, D. S.; AND MANKIN, H. J. The use of bone allografts for limb salvage in high-grade extremity osteosarcoma. Clin. Orthop. 181–196, 1991.
44. GEBHARDT, M. C.; ROTH, Y. F.; AND MANKIN, H. J. Osteoarticular allografts for reconstruction in the proximal part of the humerus after excision of a musculoskeletal tumor. J. Bone Joint Surg. Am. 72: 334–345, 1990.
45. GENDLER, E. Perforated demineralized bone matrix: a new form of osteoinductive biomaterial. J. Biomed. Mater. Res. 20: 687–697, 1986.
46. GENDLER, E. Cartilage and bone induction by artificially perforated organic bone matrix. U.S. Pat. No. 4,932,973: Jun. 12, 1990.
47. GITELIS, S.; HELIGMAN, D.; QUILL, G.; AND PIASECKI, P. The use of large allografts for tumor reconstruction and salvage of the failed total hip arthroplasty. Clin. Orthop. 62–70, 1988.
48. GITELIS, S. AND PIASECKI, P. Allograft prosthetic composite arthroplasty for osteosarcoma and other aggressive bone tumors. Clin. Orthop. 197–201, 1991.
49. GLANT, T.; HADRAZY, C.; BORDAN, L.; AND HARMATI, S. Antigenicity of bone tissue. I. Immunological and immunohistochemical study of noncollagenous proteins of the bovine cortical bone. Acta Morphol. Acad. Sci. Hung. 23: 111–122, 1975.
50. GLOWACKI, J. Cellular reactions to bone-derived material. Clinical Orthopaedics & Related Research, 47–54, 1996.
51. GLOWACKI, J. AND MULLIKEN, J. B. Demineralized bone implants. Clin. Plast. Surg. 12: 233–241, 1985.
52. GOLDBERG, V. M.; POWELL, A.; SHAFFER, J. W.; ZIKA, J.; BOS, G. D.; AND HEIPLE, K. G. Bone grafting: role of histocompatibility in transplantation. J. Orthop. Res. 3: 389404, 1985.
53. GOLDBERG, V. M. AND STEVENSON, S. Natural history of autografts and allografts. Clin. Orthop. 7–16, 1987.
54. GOWEN, M.; MACDONALD, B. R; HUGHES, D. E.; SKJODT, H.; AND RUSSELL, R. G. Immune cells and bone resorption. [Review]. Adv. Exp. Med. Biol. 208: 261–273, 1986.
55. GOWEN, M.; WOOD, D. D.; IHRIE, E. J.; MCGUIRE, M. K.; AND RUSSELL, R. G. An interleukin 1 like factor stimulates bone resorption in vitro. Nature, 306: 378–380, 1983.
56. GROSS, A. E.; ALLEN, G.; AND LAVOIE, G. Revision arthroplasty using allograft bone. Instr. Course. Lect 42: 363–380, 1993.
57. GUO, M. Z.; XIA, Z. S.; AND LIN, L. B. The mechanical and biological properties of demineralised cortical bone allografts in animals. J. Bone Joint Surg. Br. 73: 791–794, 1991.
58. HARRIS, W. H. Traumatic arthritis of the hip after dislocation and acetabular fractures: treatment by mold arthroplasty. An end-result study using a new method of result evaluation. Journal of Bone & Joint Surgery—American Volume, 51: 737–755, 1969.
59. HEERSCHE, J. N.; REIMERS, S. M.; WRANA, J. L.; WAYE, M. M.; AND GUPTA, A. K. Changes in expression of alpha 1 type 1 collagen and osteocalcin mRNA in osteoblasts and odontoblasts at different stages of maturity as shown by in situ hybridization. Proc. Finn. Dent. Soc. 88 Suppl 1: 173–182, 1992.
60. HILL, G. E. AND DROLLER, D. G. Acute and subacute deep infection after uncemented total hip replacement using antibacterial prophylaxis. Orthop. Rev. 18: 617–623, 1989.
61. HINRICHS, B.; DREYER, T.; BATTMANN, A.; AND SCHULZ, A. Histomorphometry of active osteoblast surface labelled by antibodies against non-collagenous bone matrix proteins. Bone, 14: 469472, 1993.
62. HOPKINS, K. The basic lymphocyte microcytoxicity test In The American Society of Histocompatibility and Immunogenetics Laboratory Manual, pp. 1.B.1.1.Edited by A. Nikaein. 1997.
63. HOROWITZ, M. C. AND FRIEDLAENDER, G. E. Immunologic aspects of bone transplantation. A rationale for future studies. Orthop. Clin. North Am. 18: 227–233, 1987.
64. HOROWITZ, M. C. AND FRIEDLAENDER, G. E. Induction of specific T-cell responsiveness to allogeneic bone. J. Bone Joint Surg. Am. 73: 1157–1168, 1991.
65. HORY, B.; RACADOT, E.; SAINT HILLIER, Y.; PETERS, A.; AND PEROL, C. Soluble interleukin-2 receptors in chronic renal failure. Am. J. Nephrol. 11: 276–280, 1991.
66. HOSNY, M. AND SHARAWY, M. Osteoinduction in young and old rats using demineralized bone powder allografts. J. Oral Maxillofac. Surg. 43: 925–931, 1985.
67. HOSNY, M. AND SHARAWY, M. Osteoinduction in rhesus monkeys using demineralized bone powder allografts. J. Oral Maxillofac. Surg. 43: 837–844, 1985.
68. INSALL, J. N.; RANAWAT, C. S.; AGLIETNI, P.; AND SHINE, J. A comparison of four models of total knee-replacement prostheses. Journal of Bone & Joint Surgery—American Volume, 58: 754–765, 1976.
69. JAFFE, K. A.; MORRIS, S. G.; SORRELL, R. G.; GEBHARDT, M. C.; AND MANKIN, H. J. Massive bone allografts for traumatic skeletal defects. South. Med. J. 84: 975–982, 1991.
70. JOFE, M. H.; GEBHARDT, M. C.; TOMFORD, W. W.; AND MANKIN, H. J. Reconstruction for defects of the proximal part of the femur using allograft arthroplasty. J. Bone Joint Surg. Am. 70: 507–516, 1988.
71. JOHNSON, M. E. AND MANKIN, H. J. Reconstructions after resections of tumors involving the proximal femur. Orthop. Clin. North Am. 22: 87–103, 1991.
72. KABAN, L. B.; MULLIKEN, J. B.; AND GLOWACKI, J. Treatment of jaw defects with demineralized bone implants. J. Oral Maxillofac. Surg. 40: 623–626, 1982.
73. KAMINSKA, G.; KAMINSKI, M.; AND KOMENDER, A. Immunogenicity of fresh and preserved cortical and cancellous allogeneic bone grafts as tested by modified migration inhibition test in mice. Arch. Immunol. Ther. Exp. Warsz. 26: 1053–1057, 1978.
74. KATIAPURAM, S. V.; PHILLIPS, W. C.; AND MANKIN, H. J. Giant cell tumor of bone: radiographic changes following local excision and allograft replacement Radiology, 161: 493–498, 1986.
75. KIM, Y. H. AND FRANKS, D. J. Cementless revision of cemented stem failures associated with massive femoral bone loss. A technical note. Orthop. Rev. 21: 375–380, 1992.
76. KONDO, K. AND NAGAYA, I. Bone incorporation of frozen femoral head allograft in revision total hip replacement. Nippon. Seikeigeka. Gakkai. Zasshi. 67: 408416, 1993.
77. KOSKINEN, E. V. Wide resection of primary tumors of bone and replacement with massive bone grafts: an improved technique for transplanting allogeneic bone grafts. Clin. Orthop. 302–319, 1978.
78. KUBENS, B. S.; ARNETT, K. L.; ADAMS, E. J.; PARHAM, P.; AND GROSSEWILDE, H. Definition of a new HLA-B7 subtype (B*0704) by isoelectric focusing, family studies and DNA sequence analysis. Tissue Antigens, 45: 322–327, 1995.
79. KUBENS, B. S.; KRUMBACHER, K.; AND GROSSE-WILDE, H. Biochemical definition of DLA-A and DLA-B gene products by one-dimensional isoelectric focusing and immunoblotting. European Journal of Immunogenetics, 22: 199–207, 1995.
80. KUMAGAI, J.; SARKAR, K.; AND UHTHOFF, H. K. The collagen types in the attachment zone of rotator cuff tendons in the elderly: an immunohistochemical study. Journal of Rheumatology, 21: 2096–2100, 1994.
81. KUMAGAI, J.; SARKAR, K.; UHTHOFF, H. K.; OKAWARA, Y.; AND OOSHIMA, A. Immunohistochemical distribution of type I, II and III collagens in the rabbit supraspinatus tendon insertion. Journal of Anatomy, 185: 279–284, 1994.
82. LAI, K. N.; LEUNG, J. C.; AND LAI, F. M. Soluble interleukin 2 receptor release, interleukin 2 production, and interleukin receptor expression in actvated T-lymphocytes in vitro. Pathology. 23: 224–228, 1991.
83. LANGER, F.; CZITROM, A.; PRITZKER, K. P.; AND GROSS, A. E. The immunogenicity of fresh and frozen allogeneic bone. J. Bone Joint Surg. Am. 57: 216–220, 1975.
84. LANGER, F. AND GROSS, A. The clinical and immunological assessment of frozen bone allografts. Acta Med. Pol. 19: 271–275, 1978.

85. LEE, P. H.; CHUNG, Y. C.; HU, R. H.; HUANG, M. T.; CHAO, S. H.; LEE, C. J.; AND LEE, C. S. Serum interleukin-2 and soluble interleukin-2 receptor in renal transplant recipients. J. Formos. Med. Assoc. 91: 844–848, 1992.
86. LEVENSPIEL, O. Chemical Reaction Engineering. New York. J. Wiley & Sons. 1972.
87. LEWANDROWSKI, K. U.; EKKERNKAMP, A.; MUHR, G.; AND TOMFORD, W. W. Osteoinduction in cortical bone grafts by controlled partial demineralization and laser-perforation. Transactions of the European Surgical Research Society, 1: 51996. (Abstract)
88. LEWANDROWSKI, K. U.; EKKERNKAMP, A.; TOMFORD, W. W.; AND MUHR, G. T-Zell Aktivierung nach allogener Knochentransplantation. Langenbecks Archiev fur Chirurgie. Suppl. II, 12481996.
89. LEWANDROWSKI, K. U.; SCHOLLMEIER, G.; EKKERNKAMP, A.; GROSSE-WILDE, P.; REBMANN, V.; AND TOMFORD, W. W. Immune response to laser-perforated and partially demineralized cortical bone allografts. In Preparation, 1998.
90. LEWANDROWSKI, K. U.; SCHOLLMEIER, G.; EKKERNKAMP, A.; MUHR, G.; UHTHOFF, H. K.; AND TOMFORD, W. W. Incorporation of laser-perforated and partially demineralized cortical bone allografts. Part II: A biomechanical study in sheep. In Preparation, 1998.
91. LEWANDROWSKI, K. U.; SCHOLLMEIER, G.; UHTHOFF, H. K.; AND TOMFORD, W. W. Mechanical properties of laser-perforated and partially demineralized diaphyseal bone allografts. Clin. Orthop. In Press, 1998.
92. LEWANDROWSKI, K. U.; TOMFORD, W. W.; MANKIN, H. J.; SCHOMACKER, K. T.; AND DEUTSCH, T. F. Enhancement of inforporation of cortical bone grafts by partial demineralization and laser-perforation. Transactions of the Orthopaedic Research Society, 1: 871995. (Abstract)
93. LEWANDROWSKI, K. U.; TOMFORD, W. W.; SCHOMACKER, K. T.; DEUTSCH, T. F.; AND MANKIN, H. J. Enhancement of incorporation of cortical bone grafts by controlled partial demineralization and laser-perforation. Journal of Orthopaedic Research, 15: 748–756, 1997.
94. LEWANDROWSKI, K. U.; TOMFORD, W. W.; SPRINGFIELD, D. S.; AND MANKIN, H. J. MHC-Restriktion zytotoxischer Antikörper nach Transplantation allogener Knochentransplantate. Langenbecks Archiev für Chirurgie. Suppl. 1: 157–162, 1996.
95. LEWANDROWSKI, K. U.; TOMFORD, W. W.; YEADON, A.; DEUTSCH, T. F.; MANKIN, H. J.; AND UHTHOFF, H. K. Flexural rigidity in partially demineralized diaphyseal bone grafts. Clinical Orthopaedics & Related Research, 317:254–262, 1995.
96. LEWANDROWSKI, K. U.; VENUGOPALAN, V.; TOMFORD, W. W.; SCHOMACKER, K. T.; MANKIN, H. J.; AND DEUTSCFI, T. F. Kinetics of cortical bone demineralization. A new method for nodifying cortical bone allografts. Journal Biomedical Materials and Research, 31: 365–372, 1996.
97. LIAN, J. B.; MCKEE, M. D.; TODD, A. M.; AND GERSTENFELD, L. C. Induction of bone-related proteins, osteocalcin and osteopontin, and their matrix ultrastructural localization with development of chondrocyte hypertrophy in vitro. J. Cell Biochem. 52: 206–219, 1993.
98. LORD, C. F.; GEBHARDT, M. C.; TOMFORD, W. W.; AND MANKIN, H. J. Infection in bone allografts. Incidence, nature, and treatment. J. Bone Joint Surg. Am. 70: 369–376, 1988.
99. MAHOMED, M. N.; BEAVER, R. J.; AND GROSS, A. E. The long-term success of fresh, small fragment osteochondral allografts used for intraarticular post-traumatic defects in the knee joint Orthopedics. 15: 1191–1199, 1992.
100. MAKAREWICZ, P. J.; HARASTA, L.; AND WEBB, S. L. Kinetics of acid diffusion and demineralization of bone. J. Photographic Science, 22: 148–159, 1980.
101. MALCUS, C.; POUTEIL-NOBLE, C.; TOURAINE, F.; RAFFAELE, P.; AND TOURAINE, J. L. plasma soluble interleukin-2 receptor (sIL-2R) level and activation markers in blood in the follow-up of renal allograft patients. Transplantation Proceedings, 22, No. 4: 1865–1866, 1990.
102. MANFRO, R. C.; POHANKA, E.; TOMLANIVICH, S. J.; BENET, L. Z.; SALVATIERRA, O.; AND GAROVOY, M. R. Determination of soluble IL-2 receptors in kidnez graft recipients—a 6-month follow-up. Transplant Proc. 22, No. 4: 1861–1862, 1990.
103. MANKIN, H. J.; DOPPELT, S.; AND TOMFORD, W. Clinical experience with allograft implantation. The first ten years. Clin. Orthop. 69–86, 1983.
104. MANKIN, H. J.; DOPPELT, S. H.; SULLIVAN, T. R.; AND TOMFORD, W. W. Osteoarticular and intercalary allograft transplantation in the management of malignant tumors of bone. Cancer, 50: 613–630, 1982.
105. MANKIN, H. J.; FOGELSON, F. S.; THRASHER, A. Z.; AND JAFFER, F. Massive resection and allograft transplantation in the treatment of malignant bone tumors. N. Engl. J. Med. 294: 1247–1255, 1976.
106. MANKIN, H. J.; GEBHARDT, M. C.; AND TOMFORD, W. W. The use of frozen cadaveric allografts in the management of patients with bone tumors of the extremities. Orthop. Clin. North Am. 18: 275–289, 1987.
107. MANKIN, H. J.; SPRINGFIELD, D. S.; GEBHARDT, M. C.; AND TOMFORD, W. W. Current status of allografting for bone tumors. Orthopedics. 15: 1147–1154, 1992.
108. MARDEN, L. J.; REDDI, A. H.; AND HOLLINGER, J. O. Growth and differentiation factors: role in bone induction and potential application in craniofacial surgery. J. Craniofac. Surg. 1: 154–160, 1990.
109. MARTIN, W. R. AND SUTHERLAND, C. J. Complications of proximal femoral allografts in revision total hip arthroplasty. Clin. Orthop. 161–167, 1993.
110. MCKEE, M. D.; GLIMCHER, M. J.; AND NANCI, A. High-resolution immunolocalization of osteopontin and osteocalcin in bone and cartilage during endochondral ossification in the chicken tibia. Anat. Rec. 234: 479492, 1992.
111. MINTZER, C. M.; ROBERTSON, D. D.; RACKEMANN, S.; EWALD, F. C.; SCOTT, R. D.; AND SPECTOR, M. Bone loss in the distal anterior femur after total knee arthroplasty. Clin. Orthop. 13543, 1990.
112. MNAYMNEH, W. AND MALININ, T. Massive allografts in surgery of bone tumors. Orthop. Clin. North Am. 20:455–467, 1989.
113. MUELLER-ECKHARDT, G.; KOLZOW, S.; CONRATH, K.; AND HOFFMANN, O. HLA typing and lymphocytotoxic crossmatches using conventional techniques or immunobeads. A comparative study. Vox Sanguinis, 61: 99–105, 1991.
114. MULLIKEN, J. B.; GLOWACKI, J.; KABAN, L. B.; FOLKMAN, J.; AND MURRAY, J. E. Use of demineralized allogeneic bone implants for the correction of maxillocraniofacial deformities. Ann. Surg. 194: 366–372, 1981.

115. MULLIKEN, J. B.; KABAN, L. B.; AND GLOWACKI, J. Induced osteogenesis—the biological principle and clinical applications. J. Surg. Res. 37: 487496, 1984.

116. MUSCOLO, D. L.; CALETTI, E.; SCHAJOWICZ, F.; ARAUJO, E. S.; AND MAKINO, A. Tissue-typing in human massive allografts of frozen bone. J. Bone Joint Surg. Am. 69: 583–595, 1987.

117. MUSCOLO, D. L.; KAWAI, S.; AND RAY, R. D. Cellular and humoral immune response analysis of bone-allografted rats. J. Bone Joint Surg. Am. 58: 826–832, 1976.

118. MUSCOLO, D. L.; KAWAI, S.; AND RAY, R. D. In vitro studies of transplantation antigens present on bone cells in the rat. J. Bone Joint Surg. Br. 59: 342–348, 1977.

119. NARANG, R.; WELLS, H.; AND LASKIN, D. M. Experimental osteogenesis with demineralized allogeneic bone matrix in extraskeletal sites. J. Oral Maxillofac. Surg. 40: 133–141, 1982.

120. NISBET, N. W. Antigenicity of bone. J. Bone Joint Surg. Br. 59: 263–266, 1977.

121. NUSS, F C.; FABIAN, R. L.; SARKAR, F; AND PULIAFITO, C. A. Infrared laser bone ablation. Lasers. Surg. Med. 8: 381–391, 1988.

122. O'DONNELL, R. J.; DEUTSCH, T. F.; FLOTfE, T. J.; LORENTE, C. A.; TOMFORD, W. W.; MANKIN, H. J.; AND SCHOMACKER, K. T. Effect of Er:YAG laser holes on osteoinduction in demineralized rat calvarial allografts. J. Orthop. Res. 14: 108–113, 1996.

123. ODA, Y.; SATO, H.; KAZAMA, T.; ISHII, T.; SATO, M.; SHIRANO, T.; KUDO, I.; IWASE, T.; AND MORO, I. A preliminary report on bone transplantation. 1. An immunohistochemical study on the distribution and proportions of lymphocyte subsets in lymphoid organs of nomial rats. J. Nihon. Univ. Sch. Dent 29: 303–313, 1987.

124. OLERUP, O. AND ZETTERQUIST, H. HLA-DR typing by PCR amplification with sequence-specific primers (PCR-SSP) in 2 hours: an alternative to serological DR typing in clinical practice including donor-recipient matching in cadaveric transplantation [see comments]. Tissue Antigens, 39: 225–235, 1992.

125. PAK, J. H.; PAPROSKY, W. G.; JABLONSKY, W. S.; AND LAWRENCE, J. M. Femoral strut allografts in cementless revision total hip arthroplasty. Clin. Orthop. 172–178, 1993.

126. PLAZA, J. J.; BLUM, G.; ORITZ, A.; HERNANDO, L.; FEIJOO, E.; SANZ, J.; GARCIA, R.; EGIDO, R.; AND ORITZ, F. Usefulness of serum interleukin 2 receptor levels in renal allograft recipients. Transplant. Proc. 24, No. 1: 63–64, 127. POWER, R. A.; WOOD, D. J.; TOMFORD, W. W.; AND MANKIN, H. J. Revision osteoarticular allograft transplantation in weight-bearing joints. A clinical review. J. Bone Joint Surg. Br. 73: 595–599, 1991.

128. RAISZ, L. G. Mechanisms and regulation of bone resorption by osteoclastic cells. In Disorders of bone and mineral metabolism. pp. 287–311. Edited by F. L. Coe and M. J. Fauvus. New York, Raven Press Ltd. 1992.

129. REBMANN, V.; KUBENS, B. S.; FERENCIK, S.; AND GROSSE-WILDE, H. Biochemical analysis of HLA-DP gene products by isoelectric focusing and comparison with cellular and molecular genetic typing results. Experimental & Clinical Immunogenetics, 12: 3647, 1995.

130. RIES, M. D.; GOMEZ, M. A.; ECKHOFF, D. G.; LEWIS, D. A.; BRODIE, M. R.; AND WIEDEL, J. D. An in vitro study of proximal femoral allograft strains in revision hip arthroplasty. Med. Eng. Phys. 16: 292–296, 1994.

131. RODRIGO, J. J.; FULLER, T. C.; AND MANKIN, H. J. Cytotoxic HLA-anitbodies in patients with bone and cartiage allografts. Trans. Orthop. Res. Soc. 1: 1311976.

132. SALYER, K. E.; GENDLER, E.; MENENDEZ, J. L.; SIMON, T. R.; KELLY, K. M.; AND BARDACH, J. Demineralized perforated bone implants in craniofacial surgery. J. Craniofac. Surg. 3: 55–62, 1992.

133. SCANLON, C. E. Analysis of laser-textured, demineralized bone allografts [Master's thesis]. Chicago, Northwestern University, Biomedical Engineering Department, Mar. 27: 1991.

134. SCHROEDER, T.; HELING, T.; MCKENNA, R.; RUSH, D.; JEFFREY, J.; BREWER, B.; MARTIN, L.; TRAZLOR, D.; FISHER, R. A.; FIRST, M. R.; AND MUTH, K. L. A multicenter study to evaluate a novel assay for quantilation of suluble interleukin 2 receptor in renal transplant recipients. Transplant. Proc. 53, No. 1: 3440, 1992.

135. SEPE, W. W.; BOWERS, G. M.; LAWRENCE, J. J.; FRIEDLAENDER, G. E.; AND KOCH, R. W. Clinical evaluation of freeze-dried bone allografts in periodontal osseous defects—part II. J. Periodontol. 49: 9–14, 1978.

136. SHIGETOMI, M.; KAWAI, S.; AND FUKUMOTO, T. Studies of allotransplantation of bone using immunohistochemistry and radioimmunoassay in rats. Clin. Orthop. 345–351, 1993.

137. SIRES, B. S. Bone allograft material and method. U.S. Pat. No. 5,112,354: May 12, 1992.

138. SONIS, S. T.; KABAN, L. B.; AND GLOWACKI, J. Clinical trial of demineralized bone powder in the treatment of periodontal defects. J. Oral Med. 38: 117–122, 1983.

139. SPECTOR, M. Historical review of porous-coated implants. J. Arthroplasty, 2: 163–177, 1987.

140. STEVENSON, S. The immune response to osteochondral allogralts in dogs. J. Bone Joint Surg. Am. 69: 573–582, 1987.

141. STEVENSON, S.; DANNUCCI, G. A.; SHARKEY, N. A.; AND POOL, R. R. The fate of articular cartilage after transplantation of fresh and cryopreserved tissue-antigen-matched and mismatched osteochondral allografts in dogs. J. Bone Joint Surg. Am. 71: 1297–1307, 1989.

142. STEVENSON, S.; HOHN, R. B.; AND TEMPLETON, J. W. Effects of tissue antigen matching on the healing of fresh cancellous bone allografts in dogs. Am. J. Vet Res. 44: 201–206, 1983.

143. STEVENSON, S. AND HOROWITZ, M. The response to bone allografts. J. Bone Joint Surg. Am. 74: 939–950, 1992.

144. STEVENSON, S.; LI, X. Q.; AND MARTIN, B. The fate of cancellous and cortical bone after transplantation of fresh and frozen tissue-antigen-matched and mismatched osteochondral allografts in dogs. J. Bone Joint Surg. Am. 73: 1143–1156, 1991.

145. THORNHILL, T. S.; OZUNA, R. M.; SHORTKROFF, S.; KELLER, K.; SLEDGE, C. B.; AND SPECTOR, M. Biochemical and histological evaluation of the synovial-like tissue around failed (loose) total joint replacement prostheses in human subjects and a canine model. Biomaterials, 11: 69–72, 1990.

146. TOMFORD, W. W.; BLOEM, R. M.; AND MANKIN, H. J. Osteoarticular allografts. Acta Orthop. Belg. 57 Suppl 2:98–102, 1991.

147. TOMFORD, W. W.; SCRACHAR, N. S.; FULLER, T. C.; HENRY, W. B.; AND MANKIN, H. J. Immunogenicity of frozen osteoarticular allografts. Transplant. Proc. 13: 888–890, 1981.
148. TOMFORD, W. W.; SPRINGFIELD, D. S.; MANKIN, H. J.; HUNG, H. H.; LEWANDROWSKI, K. U.; AND FULLER, T. C. The immunology of large frozen bone allograft transplantation in humans. Antibody and T-Lymphocyte response and their effects on results. Trans. Orthop. Res. Soc. 39: 1021994.
149. TOMFORD, W. W.; STARKWEATHER, R. J.; AND GOLDMAN, M. H. A study of the clinical incidence of infection in the use of banked allograft bone. J. Bone Joint Surg. Am. 63: 244–248, 1981.
150. TOMFORD, W. W.; THONGPHASUK, J.; MANKIN, H. J.; AND FERRARO, M. J. Frozen musculoskeletal allografts. A study of the clinical incidence and causes of infection associated with their use. J. Bone Joint Surg. Am. 72: 1137–1143, 1990.
151. URIST, M. R. Bone: formation by autoinduction. Science, 150: 893–899, 1965.
152. URIST, M. R.; DELANGE, R. J.; AND FINERMAN, G. A. Bone cell differentiation and growth factors. Science, 220: 680–686, 1983.
153. URIST, M. R.; SILVERMAN, B. F.; BURING, K.; DUBUC, F. L.; AND ROSENBERG, J. M. The bone induction principle. Clin. Orthop. 53: 243–283, 1967.
154. UROVITZ, E. P.; LANGER, F.; AND GROSS, A. E. Cell-mediated immunity in patients followingjoint allografting. Trans. Orthop. Res. Soc. 1: 1321976.
155. VANDERSTEENHOVEN, J. J. AND SPECTOR. M. Histological investigation of bone induction by demineralized allogeneic bone matrix: a natural biomaterial for osseous reconstruction. J. Biomed. Mater. Res. 17: 1003–1014, 1983.
156. WALSH, J. T., JR.; FLOTTE, T. J.; AND DEUTSCH, T. F. Er:YAG laser ablation of tissue: effect of pulse duration and tissue type on thermal damage. Lasers. Surg. Med. 9: 314–326, 1989.
157. WANG, E. A.; ROSEN, V.; CORDES, P.; HEWICK, R. M.; KRIZ, M. J.; LUXENBERG, D. P.; SIBLEY, B. S.; AND WOZNEY, J. M. Purification and characterization of other distinct bone-inducing factors. Proc. Natl. Acad. Sci. U.S.A 9484–9488, 1988.
158. WANG, H. [Study of antibody against protein in human allografts of decalcified bones]. Chung. Hua. Wai. Ko. Tsa. Chih. 31: 177–180, 1993.
159. WANG, J. W. AND SHIH, C. H. Allograft transplantation in aggressive or malignant bone tumors. Clin. Orthop. 203–209, 1993.
160. WATROUS, D. A. AND ANDREWS, B. S. The metabolism and immunology of bone. Semin. Arthritis Rheum. 19: 45–65, 1989.
161. WEZEMAN, F. H. AND RAY, R. D. Effects of immune environments upon bone in vitro. I. Cytotoxicity of antibodies to bone homogenates. Clin. Orthop. 93: 297–306, 1973.
162. WOZNEY, J. M. Bone morphogenetic proteins. Prog. Growth Factor. Res. 1: 267–280, 1989.
163. WOZNEY, J. M. The bone morphogenetic protein family and osteogenesis. Mol. Reprod. Dev. 32: 160–167, 1992.
164. WOZNEY, J. M.; ROSEN, V.; BYRNE, M.; CELESTE, A. J.; MOUTSATSOS, I.; AND WANG, E. A. Growth factors influencing bone development J. Cell Sci. Suppl. 13: 149–156, 1990.
165. WOZNEY, J. M.; ROSEN, V.; CELESTE, A. J.; MITSOCK, L. M.; WHITTERS, M. J.; KRIZ, R. W.; HEWICK, R. M.; AND WANG, E. A. Novel regulators of bone formation: molecular clones and activities. Science, 242: 1528–1534, 1988.
166. YOUNG, M. F.; KERR, J. M.; IBARAKI, K.; HEEGAARD, A. M.; AND ROBEY, P. G. Structure, expression, and regulation of the major noncollagenous matrix proteins of bone. Clin. Orthop. P 27594, -94. 1992.
167. YU, H. AND FERRIER, J. Interleukin-1 alpha induces a sustained increase in cytosolic free calcium in cultured rabbit osteoclasts. Biochem. Biophys. Res. Commun. 191: 343–350, 1993.
168. ZHENG, M. H.; WOOD, D. J.; AND PAPADIMITRIOU, J. M. What's new in the role of cytokines on osteoblast proliferation and differentiation? Pathol. Res. Pract. 188: 1104–1121, 1992.

Laurencin C. T et al., Tissue engineered hone-regeneration using degradable polymers: the formation of mineralized matrices. Bone. 19(1 Suppl):98S–99S, 1996

Puelacher W. C. et al., Femoral shaft reconstruction using tissue-engineered growth of bone. International Journal of Oral and Maxillofacial Surgery. 25(3):223–8, 1996

Reddi A. H., Role of morphogenentic proteins in skeletal tissue engineering and regeneration. Nature Biotechnology. 16(3):247–52, 1998

Wintermantel E. et al., Tissue engineering scaffolds using superstructures. Biomaterials. 17(2):83–91, 1996.

Brittberg et al., Treatmrent of deep cartilage defects in the knee with autologous chondrocyte transplantation. N. Eng. J. M. 331:889–895, 1994.

Reddi, A. H. et al., Influence of geometry of transplanted tooth and bone on transformation of fibroblasts. Proc. Soc. Exp. Biol. Med. 143:634–637, 1973.

Nakahara et al., Culture-expanded human periosteal derived cells exhibit osteochondrol potential in vivo. J. Orthop. Res. 9:465–476, 1991.

What is claimed is:

1. A biocompatible transplant comprising an isolated and modified bone substrate formed into a suitable shape having a porous coating thereon formed of a biocompatible biodegradable polymer, wherein cells capable of regenerating autologous tissue are seeded onto the surface of the polymer coating to form the transplant.

2. The transplant of claim 1, comprising periosteal cells.

3. The transplant of claim 1, wherein the biocompatible biodegradable polymer coating promotes ingrowth of tissues at a site of transplantation.

4. The transplant of claim 3, wherein the biocompatible biodegradable polymer coating promotes ingrowth of bone cells or blood vessels.

5. The transplant of claim 1 wherein the coating is seeded with autologous periosteal cells from the intended graft recipient.

6. The transplant of claim 5, wherein the substrate further comprises a material selected from the group consisting of a resorbably precured bone cement, a molecularly reinforced interpenetrating polymeric network and a molded bioerodible polymer.

7. The transplant of claim 4 wherein the transplant is for bone replacement and the biocompatible biodegradable polymer coating is between 0.5 and 2.0 mm in thickness.

8. The transplant of claim 1 wherein the substrate is formed of isolated modified donor bone.

9. The transplant of claim 1 wherein the bone is demineralized.

10. The transplant of claim 1 wherein the biocompatible polymer coating is a foam.

11. The transplant of claim 8 wherein the porosity of the bone has been increased.

* * * * *